US008338468B2

(12) United States Patent
Wingenfeld et al.

(10) Patent No.: US 8,338,468 B2
(45) Date of Patent: Dec. 25, 2012

(54) MICROBICIDAL COMPOSITION

(75) Inventors: Andrea Wingenfeld, Lauben (DE); Christiane Ochs, Memmingen (DE)

(73) Assignee: ISP Investments Inc., Wilmington, DE (US)

( * ) Notice: Subject to any disclaimer, the term of this patent is extended or adjusted under 35 U.S.C. 154(b) by 1103 days.

(21) Appl. No.: 11/994,854

(22) PCT Filed: Jun. 30, 2006

(86) PCT No.: PCT/US2006/025976
§ 371 (c)(1),
(2), (4) Date: Jul. 16, 2008

(87) PCT Pub. No.: WO2007/008484
PCT Pub. Date: Jan. 18, 2007

(65) Prior Publication Data
US 2009/0143341 A1    Jun. 4, 2009

Related U.S. Application Data

(60) Provisional application No. 60/697,681, filed on Jul. 8, 2005.

(30) Foreign Application Priority Data

Jul. 29, 2005 (DE) .......................... 10 2005 036 314

(51) Int. Cl.
*A01N 43/80* (2006.01)
*A61K 31/425* (2006.01)

(52) U.S. Cl. ...................................... 514/372; 424/405

(58) Field of Classification Search ........................ None
See application file for complete search history.

(56) References Cited

U.S. PATENT DOCUMENTS

2004/0265261 A1 * 12/2004 Kohut et al. ............... 424/70.16

FOREIGN PATENT DOCUMENTS

| EP | 1332675 | | 8/2003 |
|---|---|---|---|
| GB | 2315747 | * | 2/1998 |
| JP | 2000290205 | * | 10/2000 |
| JP | 2001048720 | * | 2/2001 |

OTHER PUBLICATIONS

Matissek, Use and analysis of 2-methyl-3(2H)-isothiazoline and 5-chloro-2-methyl-3(2H)-isothiazolone as preservatives in cosmetics, GIT-supplement, 1987, (7), 5-6,8-12.*
International Search Report and Written Opinion issued regarding International Application No. PCT/US06/25976 (Feb. 20, 2007).
Matissek, R., "Use and analysis of 2-methyl-3(2H)-isothiazoline and 5-chloro-2-methyl-3(3H)-isothiazole as preservatives in cosmetics," GIT-Supplement, 1987, (7), pp. 5-6, 8-12, ABS.

* cited by examiner

*Primary Examiner* — Alton Pryor
(74) *Attorney, Agent, or Firm* — William J. Davis; Thompson Hine LLP

(57) ABSTRACT

The invention relates to a microbicidal composition which comprises a mixture of at least two components, the first component being 2-methyl-3-isothiazolone (MIT) and the second component being at least one active compound selected from the following groups of active compounds: a) compound having activated methylol groups b) quats or polyquats c) carbamates d) organic acids e) aromatic alcohols.

16 Claims, No Drawings

MICROBICIDAL COMPOSITION

The invention relates to a microbicidal composition which comprises a mixture of at least two components, the first component being 2-methyl-3-isothiazolone (MIT).

MIT is also described by the CAS No. 2682-20-4.

The abovementioned microbicidal compositions have been disclosed, for example, by European patent 1 332 675 in which a commercially available microbicidal benzoic acid is used as second component.

The combination described in this European patent restricts the application of MIT with respect to the pH range.

It is an object of the present invention to provide microbicidal compositions as described above whose application is possible in as wide a pH range as possible.

To achieve this object the invention proceeds from a microbicidal composition as described at the outset and proposes that this comprises a mixture of at least two components, the first component being 2-methyl-3-isothiazolone and the second component being at least one active compound selected from the following groups of active compounds:

a) compounds having activated methylol groups
b) quats or polyquats
c) carbamates
d) organic acids
e) aromatic alcohols The abovementioned groups of active compounds are in each case likewise biocidal or microbicidal. They frequently have an altered antimicrobial spectrum. Precisely in combination with MIT, resultant synergistic effects are produced thereby, since a greater bandwidth of organisms can be actively combated. The selection of the proposed active compounds is such that they can also be used in a wide pH range in accordance with the desired use. The invention therefore combines a broad antimicrobial activity spectrum with a wide pH application range.

In particular, it is proposed that the inventive composition is usable, for example, in the pH range from 4 to 10.

Different active compounds also have a different mechanism of action. This therefore results in the fact that, for example, one variety of organisms can be attacked by various active compound mechanisms and a synergistic effect can also thus be produced.

The inventive microbicidal composition is used in domestic products, for example cleaners, dishwashing agents, cleaning agents, cosmetic products, shampoos, soaps, wet wipe uses, for example using moist cloths and the like. Likewise, the inventive composition can also be used in industrial applications, for example in coatings, paints, plasters, emulsions, dispersions, glues, latex and the like.

It is proposed according to the invention that the composition is a mixture of at least two components. The invention does not exclude the microbicidal composition also having more than two components, MIT then being combinable with two or more further active compounds from the said group selected compounds. It is also possible that a plurality of active compounds of one group of active compounds are used in an inventive composition. The field of application of such a microbicidal composition can thereby be further optimized and adapted for the specific application. The previously described mechanisms with respect to pH and different possibilities of attacking the harmful organisms apply here in an unmodified manner.

A preferred variant of the invention provides that the composition comprises one or more different solvents.

A variant of the invention provides that water, glycols and/or glycol ethers are provided as solvent.

A further development according to the invention proposes that a synergistic action of the components present in the mixture is provided.

A preferred variant of the invention provides that an activity enhancement is provided by the solvent, in particular the glycols and/or glycol ethers.

It has been found that the proposed solvents, without having activity of their own, improve the activity of the active compounds used. This effect is described and taken to mean hereinafter activity enhancement.

The inventive compositions are used in specific applications which contain, for example, various liquid phases. For example, in an oil-water mixture, an oil phase occurs in addition to a water phase. The harmful organisms to be attacked are situated in the water phase or the boundary layer. The use of the proposed solvents means that the active compounds also preferably remain in the aqueous phase and can destroy microorganisms there.

Improved activities of the active compounds used finally result from improved active compound uptakes into the respective organisms with the proposed solvents. The concentration of the active compounds used can be restricted, which decreases costs.

In particular, such activity enhancements have been observed with 1,2-octanediol, pentylene glycol and hexylene glycol. Generally this property, however, is assigned to the entire group of glycols or glycol ethers as solvents.

An inventive variant provides that bronopol, diazolidinylurea or imidazolidinylurea are provided as compounds having activated methylol groups.

A further development of the invention proposes that polyaminopropyl biguanide, cetrimonium bromide or benzalconium chloride are provided as quats or polyquats.

A preferred variant of the invention provides that iodopropynyl butylcarbamate or dithiocarbamate are provided as carbamates.

An inventive variant provides that dehydroacetic acid, undecylenic acid or salicylic acid are provided as organic acids.

A further development of the invention proposes that phenoxyethanol, phenylethanol, phenoxypropanol, phenylpropanol or dichlorobenzyl alcohol are provided as aromatic alcohols.

A preferred variant of the invention provides that polypropylene glycol 2-methyl ether, 1,2-octanediol, propylene glycol, pentylene glycol, hexylene glycol, dipropylene glycol, dipropylene glycol monomethyl ether, oligo- or polyethylene glycols or polypropylene glycols are provided as glycols or glycol ethers. Polypropylene glycol is also called PPG-2-methyl ether.

An inventive variant provides that the weight ratio between 2-methyl-3-isothiazolone and the other components is between 1:1000 and 200:1, preferably between 2:100 and 5:1.

As described, the use of MIT in proportion to the other component varies over a wide range. Here, in the desired field of use, an appropriate combination is possible by which, obviously, by corresponding control and skilful selection of the active compounds, the total costs of an inventive composition can be greatly reduced.

A further development of the invention proposes that the weight ratio between the components and the solvent is between 1:100 and 100:1, preferably 1:10 to 3:2.

A preferred variant of the invention provides the weight percentage of glycol or glycol ether of the composition is from 0% to 85%.

An inventive variant provides that the weight percentage of 1,2-octanediol of the composition is from 0% to 10%.

A further development of the invention proposes that the weight percentage of 2-methyl-3-isothiazolone in the composition is from 0.1% to 20%, preferably approximately 2% to 8%.

A preferred variant of the invention provides that the weight percentage of aromatic alcohols of the total composition is from 0% to 99.9%, preferably 0.1% to 80%.

An inventive variant provides that the weight percentage of water of the total composition is from 0% to 99.9%.

A further development of the invention proposes that the composition is essentially free from halogenated isothiazolone.

The microbicidal compositions of the present invention are essentially free from halogenated isothiazolones. "Essentially" free is taken to mean that the composition has from 0 to at most 3%, preferably from 0 to 1%, and further preferably from 0 to only 0.5%, halogenated isothiazolones (based on the weight), based on the combined weight of halogenated isothiazolone and MIT. A further concentration of halogenated isothiazolone is unstable and requires additional stabilization components. These can be, for example, metal salts and the like which, however, cause additional costs and also can lead to undesirable side effects in subsequent formulation. It is therefore expedient, based on the MIT, to provide a weight percentage as low as possible, as described, of halogenated isothiazolone.

In particular, the finished use formulation is sought to have at maximum a halogenated isothiazolone content of 1000 ppm.

The table below describes various exemplary samples according to the invention:

| Sample | Component | Weight percentage [%] | Components of the weight percentages [%] |
|---|---|---|---|
| 1 | MIT | 5 | 0.1 ... 20 |
|  | Diazolidinylurea | 50 | 20 ... 60 |
|  | Water | 45 | 0 ... 79.9 |
| 2 | MIT | 5 | 0.1 ... 20 |
|  | Bronopol | 10 | 0.1 ... 20 |
|  | Phenylethanol | 30 | 0 ... 80 |
|  | PPG-2-methyl ether | 35 | 0 ... 99.9 |
|  | Water | 20 | 0 ... 99.9 |
| 3 | MIT | 2-5 | 0.1 ... 20 |
|  | Phenylethanol | 50-80 | 0 ... 99.9 |
|  | 1,2-octanediol | 0-10 | 0 ... 50 |
|  | PPG-2-methyl ether | 6-30 | 0 ... 99.9 |
|  | Water | 2-15 | 0 ... 99.9 |
| 4 | MIT | 2-5 | 0.1 ... 20 |
|  | Cetrimonium bromide | 5-20 | 0.1 ... 20 |
|  | Phenylethanol | 0-76 | 0 ... 99 |
|  | 1,2-octanediol | 0-10 | 0 ... 50 |
|  | PPG-2-methyl ether | 0-35 | 0 ... 99.9 |
|  | Water | 2-85 | 0 ... 99.9 |
| 5 | MIT | 2-5 | 0.1 ... 20 |
|  | Polyaminopropyl biguanide | 10 | 0.1 ... 40 |
|  | Phenylethanol | 25-30 | 0 ... 99.9 |
|  | PPG-2-methyl ether | 15-16 | 0 ... 99.9 |
|  | Water | 42-45 | 0 ... 99.9 |
| 6 | MIT | 5 | 0.1 ... 20 |
|  | Dichlorobenzyl alcohol | 40 | 0 ... 55 |
|  | Phenylethanol | — | 0 ... 50 |
|  | PPG-2-methyl ether | 0-50 | 0 ... 99.9 |
|  | 1,2-propylene glycol | 0-50 | 0 ... 99.9 |
|  | Water | 5 | 0 ... 20 |
| 7 | MIT | 5 | 0.1 ... 20 |
|  | Iodopropynyl butylcarbamate | 5 | 0.1 ... 20 |
|  | Phenylethanol | 0-50 | 0 ... 99.9 |
|  | PPG-2-methyl ether | 0-25 | 0 ... 99.9 |
|  | 1,2-propylene glycol | 0-85 | 0 ... 99.9 |
|  | Water | 5-15 | 0 ... 99.9 |
| 8 | MIT | 5 | 0.1 ... 20 |
|  | Dehydroacetic acid | 8 | 0.1 ... 10 |
|  | Phenylethanol | 82 | 0 ... 99.9 |
|  | PPG-2-methyl ether | — | 0 ... 99.9 |
|  | 1,2-propylene glycol | — | 0 ... 99.9 |
|  | Water | 5 | 0 ... 99.9 |

The reported weight percentages relate to the total weight of the composition. The table above gives an overview of the inventive compositions which exhibit the desired properties. The table is to be taken to mean that the compositions having the reported weight percentages (in the 3rd column) lead to a stable composition.

Instead of phenylethanol, it is also provided according to the invention to use other aromatic alcohols (see their list). In addition, for the various samples in the last column a bandwidth of weight percentages of the individual components is reported. Reference is explicitly made to the fact that all combinations mentioned here are considered conjointly disclosed. If the bandwidth starts at 0%, there are also formulation proposals in which the respective component is not a member of the respective composition. However, reference is made explicitly to the fact that a small fraction, for example 0.1% of the respective component, is also explicitly considered disclosed for all respective components and to this extent an interval restricted in this respect, also, for example, from 0.1 to 99.9%, is a preferably restricted interval.

The weight percentages are to be taken to mean preferred embodiment of the invention and likewise do not restrict the more broadly worded bandwidth of the weight percentages belonging to the invention.

Synergy tests were conducted using microbiological standard methods. Ringer's Solution (Merck, VWR) was used for testing bacteria, yeast and mould species. In jars 100 ml aliquots of sterile Ringer Solution are dosed with the preservatives and a known inoculum of the single test species is added. A control sample containing no preservative is also used to ascertain the biocide effect on the inoculum. The prepared jars were incubated at 30° C. Aliquots are streaked out at regular intervals on specific nutrient agar so that an estimate of kill time can be determined at the same time as effective concentration. TSA (tryptic soy agar) was used for bacteria; MEA (malt extract agar) was used for yeast and moulds. The plates were visually evaluated for microbial growth to determine the MIC after various incubation times at 30° C.

The synergy of the combinations of the present invention was determined against four bacteria, *Pseudomonas aeruginosa, Escherichia coli, Proteus Mirabilis,* and *Staphylococcus aureus,* a yeast, *Candida albicans* and two moulds *Trichoderma viride* and *Aspergillus niger*. The single micro-organisms were used at a concentration of about $10^5$ microbes per ml. these micro-organisms are standard reference organisms and representative of natural contaminants in many consumer and industrial applications.

The test results for demonstration of synergy of the preservative combinations of the present invention are shown below. In each test first component (A) was MIT and the second component was phenylethylalcohol (B).

| Microorganism | | ppm MIT QA | MIT Qa | Phenyl-ethyl-alcohol Qb | ppm Phenyl-ethyl-alcohol QB | SI* |
|---|---|---|---|---|---|---|
| *Pseudomonas Aeruginosa* | Test 1 | 50 | 25 | 250 | 2000 | 0.63 |
| | Test 2.1 | 25 | 12.5 | 125 | 2500 | 0.55 |
| | Test 2.2 | 25 | 12.5 | 125 | 2500 | 0.55 |
| | Test 2.3 | 25 | 12.5 | 125 | 2500 | 0.55 |
| *Escherichia Coli* | Test 1 | 50 | 25 | 250 | 2000 | 0.63 |
| | Test 2.1 | 25 | 12.5 | 125 | 2500 | 0.55 |
| | Test 2.2 | 25 | 12.5 | 125 | 2500 | 0.55 |
| | Test 2.3 | 25 | 12.5 | 125 | 2500 | 0.55 |
| *Proteus mirabilis* | Test 1 | 50 | 25 | 250 | 2000 | 0.63 |
| | Test 2.1 | 25 | 12.5 | 125 | 2000 | 0.56 |
| | Test 2.2 | 25 | 12.5 | 125 | 2000 | 0.56 |
| | Test 2.3 | 25 | 12.5 | 125 | 2000 | 0.56 |
| *Staphylococcus aureus* | Test 1 | 75 | 25 | 250 | 2000 | 0.46 |
| | Test 2.1 | 50 | 25 | 250 | 1500 | 0.67 |
| | Test 2.2 | 50 | 12.5 | 125 | 1500 | 0.33 |
| | Test 2.3 | 50 | 12.5 | 125 | 1500 | 0.33 |
| *Candida albicans* | Test 1 | 50 | 25 | 250 | 2000 | 0.63 |
| | Test 2.1 | 50 | 25 | 250 | 2500 | 0.60 |
| | Test 2.2 | 50 | 25 | 250 | 1500 | 0.67 |
| | Test 2.3 | 50 | 12.5 | 125 | 1500 | 0.33 |
| *Aspergillus Niger* | Test 1 | 50 | 25 | 250 | 1500 | 0.67 |
| | Test 2.1 | 50 | 37.5 | 375 | 2000 | 0.94 |
| | Test 2.2 | 50 | 25 | 250 | 2000 | 0.63 |
| | Test 2.3 | 50 | 37.5 | 375 | 2000 | 0.94 |
| *Trichoderma viride* | Test 1 | 75 | 25 | 250 | 2000 | 0.46 |
| | Test 2.1 | 50 | 25 | 250 | 3000 | 0.58 |
| | Test 2.2 | 50 | 25 | 250 | 3000 | 0.58 |
| | Test 2.3 | 50 | 25 | 250 | 3000 | 0.58 |

*SI = Synergy Index
Formula SI = Qa/QA + Qb/QB
QA = concentration of compound A (first component in ppm, acting alone, which produced an end point (MIC of Compound A)
Qa = concentration of compound A in ppm, in the mixture, which produced an end point
QB = concentration of compound B (second component in ppm, acting alone, which produced an end point (MIC of Compound B)
Qb = concentration of compound B in ppm, in the mixture, which produced an end point
Test one was done as single test, Test 2 was performed under statistical conditions with 3 parallel samples
Result: all SI indices show values below 1 sometimes even below 0.5

Formulation Based on 2-Methyl-isothiazolin-3-one and Phenylethylalcohol

| | immediatly after preperation | | | |
|---|---|---|---|---|
| sample | sample 1 | sample 2 | sample 3 | sample 4 |
| appearance | colorless, clear liquid | colorless, clear liquid | colorless, clear liquid | colorless, clear liquid |
| smell | flowery characteristic | flowery characteristic | flowery characteristic | flowery characteristic |
| Hazen | 25 | 20 | 23 | 21 |
| Gardner content | 0 | 0 | 0 | 0 |
| 2-Methyl-isothiazolin-3-one % | 5.0 | 5.1 | 5.0 | 5.0 |
| phenylethylalcohol % | 49.8 | 49.8 | 49.7 | 49.8 |

| | 4 weeks room temperatures dark | | | | 4 weeks room temperatures on the window east side | |
|---|---|---|---|---|---|---|
| | sample 1 | sample 2 | sample 3 | sample 4 | sample 1 | sample 2 |
| appearance | colorless, clear liquid | colorless, clear liquid | colorless, clear liquid | colorless, clear liquid | colorless, clear liquid | colorless, clear liquid |
| smell | flowery characteristic | flowery characteristic | flowery characteristic | flowery characteristic | flowery characteristic | flowery characteristic |
| Hazen | 51 | 45 | 50 | 46 | 56 | 56 |
| Gardner content | 0.1 | 0.1 | 0.1 | 0.1 | 0.1 | 0.1 |
| 2-Methyl-isothiazolin-3-one % | 5.0 | 5.0 | 4.9 | 5.0 | 4.9 | 4.9 |
| phenylethylalcohol % | 49.9 | 50.2 | 50.3 | 50.1 | 49.5 | 49.3 |

| | 4 weeks room temperatures on the window east side | | 4 weeks 40° C. dark | | | |
|---|---|---|---|---|---|---|
| | sample 3 | sample 4 | sample 1 | sample 2 | sample 3 | sample 4 |
| appearance | colorless, clear liquid | colorless, clear liquid | colorless, clear liquid | colorless, clear liquid | colorless, clear liquid | colorless, clear liquid |
| smell | flowery characteristic | flowery characteristic | flowery characteristic | flowery characteristic | flowery characteristic | flowery characteristic |
| Hazen | 76 | 55 | 188 | 186 | 178 | 180 |
| Gardner content | 0.2 | 0.1 | 0.8 | 0.8 | 0.8 | 0.8 |
| 2-Methyl-isothiazolin-3-one % | 4.8 | 4.9 | 5.0 | 4.9 | 4.8 | 4.9 |
| phenylethylalcohol % | 50.2 | 49.8 | 50.8 | 49.0 | 50.6 | 50.0 |

|   | 6 months room temperatures glass cabinet sample 4 | 6 months 30° C. dark sample 4 | 6 months 8° C. dark sample 4 | 12 months room temperatures glass cabinet sample 4 | 12 months 30° C. dark sample 4 | 12 months 8° C. dark sample 4 |
| --- | --- | --- | --- | --- | --- | --- |
| appearance | colorless, clear liquid | yellowish, clear liquid | colorless, clear liquid | colorless, clear liquid | yellowish, clear liquid | colorless, clear liquid |
| smell | flowery characteristic | flowery characteristic | flowery characteristic | flowery characteristic | flowery characteristic | flowery characteristic |
| Hazen | 150 | 245 | 89 | 333 | 470 | 134 |
| Gardner | 1.0 | 1.8 | 0.3 | 1.9 | 3 | 0.8 |
| content |  |  |  |  |  |  |
| 2-Methyl-isothiazolin-3-one % | 5.03 | 4.88 | 5.05 | 4.97 | 5.01 | 5.01 |
| phenylethylalcohol % | 50.11 | 50.16 | 50.77 | 50.28 | 50.18 | 50.21 |

Formulation Based on 2-Methyl-isothiazolin-3-one, Dehydroacetic Acid and Phenylethylalcohol

|   | immediatly after preperation ||||
| --- | --- | --- | --- | --- |
| sample | sample 1 | sample 2 | sample 3 | sample 4 |
| appearance | colorless, clear liquid | colorless, clear liquid | colorless, clear liquid | colorless, clear liquid |
| smell | flowery characteristic | flowery characteristic | flowery characteristic | flowery characteristic |
| Hazen | 228 | 248 | 246 | 241 |
| Gardner | 1.1 | 1.3 | 1.2 | 1.3 |
| content |  |  |  |  |
| 2-Methyl-isothiazolin-3-one % | 5.0 | 5.1 | 5.0 | 5.0 |
| Dehydroacetic Acid % | 7.9 | 8.0 | 8.0 | 8.0 |
| phenylethylalcohol % | 81.6 | 81.6 | 81.7 | 81.7 |

|   | 4 weeks room temperatures dark |||| 4 weeks room temperatures on the window east side ||
| --- | --- | --- | --- | --- | --- | --- |
|   | sample 1 | sample 2 | sample 3 | sample 4 | sample 1 | sample 2 |
| appearance | colorless, clear liquid | colorless, clear liquid | colorless, clear liquid | colorless, clear liquid | colorless, clear liquid | colorless, clear liquid |
| smell | flowery characteristic | flowery characteristic | flowery characteristic | flowery characteristic | flowery characteristic | flowery characteristic |
| Hazen | 361 | 341 | 354 | 352 | >1000 | >1000 |
| Gardner | 2 | 1.9 | 1.9 | 1.9 | 5.1 | 4.9 |
| content |  |  |  |  |  |  |
| 2-Methyl-isothiazolin-3-one % | 4.8 | 4.9 | 4.7 | 4.8 | 4.8 | 4.9 |
| Dehydroacetic Acid % | 7.7 | 7.6 | 7.8 | 7.7 | 7.6 | 7.7 |
| phenylethylalcohol % | 81.7 | 82.5 | 82 | 81.8 | 82.0 | 82.4 |

|   | 4 weeks room temperatures on the window east side || 4 weeks 40° C. dark ||||
| --- | --- | --- | --- | --- | --- | --- |
|   | sample 3 | sample 4 | sample 1 | sample 2 | sample 3 | sample 4 |
| appearance | colorless, clear liquid | colorless, clear liquid | colorless, clear liquid | colorless, clear liquid | colorless, clear liquid | colorless, clear liquid |
| smell | flowery characteristic | flowery characteristic | flowery characteristic | flowery characteristic | flowery characteristic | flowery characteristic |
| Hazen | 965 | >1000 | 843 | 860 | 849 | 855 |
| Gardner | 4.6 | 4.8 | 4.3 | 4.3 | 4.3 | 4.4 |
| content |  |  |  |  |  |  |
| 2-Methyl-isothiazolin-3-one % | 4.8 | 4.9 | 4.4 | 4.4 | 4.1 | 4.3 |
| Dehydroacetic Acid % | 7.7 | 7.7 | 7.7 | 7.7 | 7.8 | 7.7 |
| phenylethylalcohol % | 82.1 | 82.2 | 82.3 | 82.5 | 80.7 | 81.9 |

|   | 6 months room temperatures glass cabinet sample 4 | 6 months 30° C. dark sample 4 | 6 months 8° C. dark sample 4 | 12 months room temperatures glass cabinet sample 4 | 12 months 30° C. dark sample 4 | 12 months 8° C. dark sample 4 |
| --- | --- | --- | --- | --- | --- | --- |
| appearance | colorless, clear liquid | yellowish, clear liquid | colorless, clear liquid | colorless, clear liquid | yellowish, clear liquid | colorless, clear liquid |

| smell | flowery characteristic | flowery characteristic | flowery characteristic | flowery characteristic | flowery characteristic | flowery characteristic |
|---|---|---|---|---|---|---|
| Hazen | >1000 | >1000 | 880 | >1000 | >1000 | >1000 |
| Gardner | 5.5 | 5.3 | 4.3 | 7.6 | 8.6 | 6.1 |
| content | | | | | | |
| 2-Methyl-isothiazolin-3-one % | 3.81 | 3.02 | 4.33 | 3.5 | 2.5 | 4.3 |
| Dehydroacetic Acid % | 6.8 | 5.92 | 7.38 | 6.7 | 5.6 | 7.3 |
| phenylethylalcohol % | 78.16 | 77.24 | 81.91 | 82.7 | 81.9 | 82.8 |

The invention claimed is:

1. A microbicidal composition which comprises a mixture of at least two components, the first component being 2-methyl-3-isothiazolone and the second component being phenylethanol; wherein the mixture of 2-methyl-3-isothiazolone and phenylethanol exhibits a synergistic effect.

2. The composition according to claim 1, wherein the composition comprises one or more different solvents wherein at least one solvent is selected from the group consisting of water, glycols, and glycol ethers.

3. The composition according to claim 2, wherein there is activity enhancement by the solvent.

4. The composition according to claim 2, wherein the composition comprises glycols or glycol ethers are selected from the group consisting of polypropylene glycol 2-methyl ether, 1,2-octanediol, propylene glycol, pentylene glycol, hexylene glycol, dipropylene glycol, dipropylene glycol monomethyl ether, oligo- or polyethylene glycols and polypropylene glycols.

5. The composition according to claim 1, wherein the weight ratio between 2-methyl-3-isothiazolone and phenylethanol is 1:10.

6. The composition according to claim 2, wherein the weight ratio between the components 2-methyl-3-isothiazolone and phenylethanol, and the solvent is between 1:100 and 100:1.

7. The composition according to claim 2, wherein the weight percentage of glycol or glycol ether in the composition is from 0% to 85%.

8. The composition according to claim 4, wherein the weight percentage of 1,2-octanediol in the composition is from 0% to 10%.

9. The composition according to claim 1, wherein the weight percentage of 2-methyl-3-isothiazolone in the composition is from 0.1% to 20%.

10. The composition according to claim 2, wherein the weight percentage of water in the total composition is from 0% to 99.9%.

11. The composition according to claim 1, wherein the composition is essentially free from halogenated isothiazolone.

12. The composition according to claim 1, wherein the weight ratio between 2-methyl-3-isothiazolone and phenylethanol is 1:10.

13. The composition according to claim 2, wherein the weight ratio between the components, 2-methyl-3-isothiazolone and phenylethanol, and the solvent is between 1:10 to 3:2.

14. The composition according to claim 1, wherein the weight percentage of 2-methyl-3-isothiazolone in the composition is from 2% to 8%.

15. The composition according to claim 1, wherein the weight percentage of phenylethanol in the total composition is from 0.1% to 80%.

16. The composition according to claim 15, wherein the weight percentage of 2-methyl-3-isothiazolone in the composition is from 2% to 8%.

* * * * *